United States Patent [19]

Gracovetsky et al.

[11] Patent Number: 5,022,412
[45] Date of Patent: Jun. 11, 1991

[54] CONNECTION KIT FOR SKIN-MARKERS AND ELECTRODES

[75] Inventors: Serge Gracovetsky, St Lambert; Rudolf U. Frost, Montreal, both of Canada

[73] Assignee: Diagnospine Research Inc., Montreal, Canada

[21] Appl. No.: 247,360

[22] Filed: Sep. 21, 1988

[30] Foreign Application Priority Data

Oct. 5, 1987 [CA] Canada ................................. 548628

[51] Int. Cl.⁵ .............................................. A61B 5/103
[52] U.S. Cl. ................................. 128/781; 128/639; 128/644; 128/384
[58] Field of Search ............... 128/781, 782, 733, 639, 128/644, 802, 799, 783, 384, 383

[56] References Cited

U.S. PATENT DOCUMENTS

| 792,066 | 6/1905 | McGregor | 128/802 |
|---|---|---|---|
| 1,498,059 | 6/1924 | Tyler | 128/802 |
| 3,409,007 | 11/1968 | Fuller | 128/644 |
| 3,802,698 | 4/1974 | Burian et al. | 128/644 |
| 4,026,278 | 5/1977 | Ricketts et al. | 128/644 |
| 4,493,328 | 1/1985 | Saito | 128/782 |
| 4,655,227 | 4/1987 | Gracovetsky | 128/781 |
| 4,664,130 | 5/1987 | Gracovetsky | 128/781 |
| 4,669,479 | 6/1987 | Dunseath, Jr. | 128/644 |
| 4,699,156 | 10/1987 | Gracovetsky | 128/781 |

FOREIGN PATENT DOCUMENTS 2111832 7/1983 United Kingdom ................ 128/799

Primary Examiner—William E. Kamm
Assistant Examiner—Scott M. Getzow
Attorney, Agent, or Firm—ROBIC

[57] ABSTRACT

A connection kit for use in electrically connecting to a monitoring equipment a plurality of skin-markers and-/or electrodes detachably fixed onto the body of a patient, in such a manner as to let the patient free to move in a given area. The kit comprises a connection box electrically connectable to the monitoring equipment in such a manner as to let the patient free to move in the given area. It also comprises a harness to be worn by the patient. The harness includes a chest-piece on which can be mounted the connection box. At least one primary conductor cable is provided, which has one end electrically connectable to the connection box and at least one other end provided with a connecting plug. This connection plug is detachably fixable with a sticking pad. Alternatively, the connection plug may be fixed in the same position on a back-strap forming part of the harness and passing over shoulder of the patient. At least one secondary conductor cable is also provided, which has one end electrically connectable to the connecting plug of the primary cable, and at least one other end electrically connectable to at least one skin-marker and/or electrode.

8 Claims, 5 Drawing Sheets

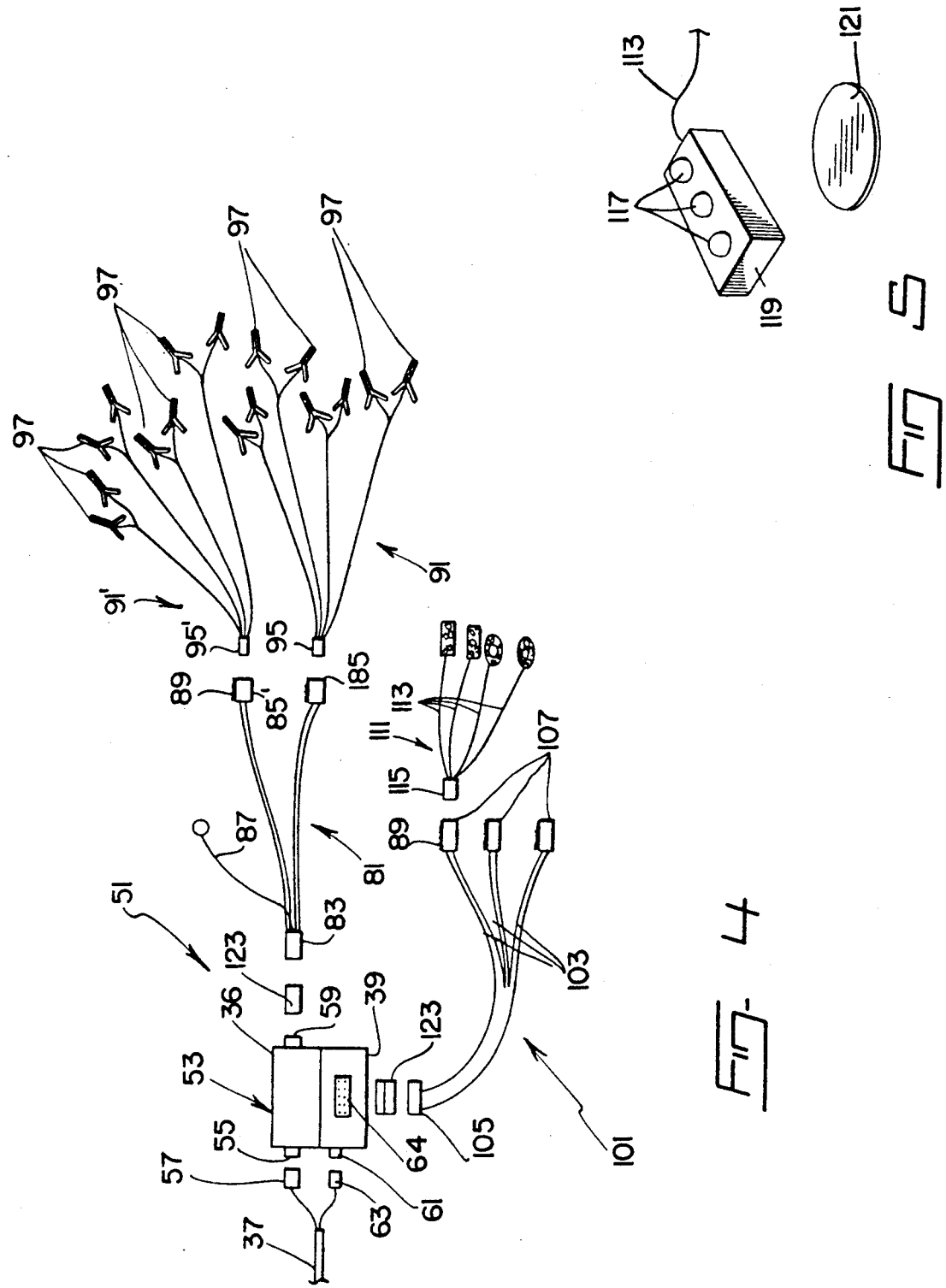

CONNECTION KIT FOR SKIN-MARKERS AND ELECTRODES

BACKGROUND OF THE INVENTION a) Field of the Invention

The present invention relates to a connection kit for use in electrically connecting to a monitoring equipment, a plurality of skin-markers and/or electrodes detachably fixed onto the body of a patient, in such a manner as to let the patient free to move in a given area.

More particularly, the invention relates to a connection kit of the above-mentioned type, that can be used for carrying out the very specific methods for the evaluation of the flexibility of the spine of a patient and/or detection of any mechanical injury in the lumbar portion thereof, as disclosed and claimed in U.S. Pat. Nos. 4.655.227; 4.664.130 and 4.669.156 and co-pending U.S. Pat. application Ser. No. 250,215 filed on Sept. 28, 1988, all granted to DIAGNOSPINE RESEARCH INC.

b) Brief Description of the Prior Art

It is of common practice in the medical art, to use skin-markers and/or electromyographic (EMG) electrodes to evaluate in a non-invasive manner the physical condition of a patient and to detect any abnormal response that may be significative of a disease.

By way of example, the method and equipment disclosed and claimed in the above referenced U.S. patent application No. 250,215, make use of a plurality of separate, dot-sized skin-markers each consisting of at least one LED attachable to the skin of the back of the patient including his arms and legs, and a set of surfaces electrodes also attachable to the skin of the patient's back for tracking the special position of the patient and measuring the electromyographic (EMG) activities of his muscles while he is performing a given exercice, such as flexing forward in the sagittal plane or bending laterally in the frontal plane. The data that are so collected, are then processed and may be used to evaluate the flexibility of the spine of a patient and to detect the presence of a possible mechanical injury in the lumbar portion of this spine.

Of course, the skin-markers and EMG electrodes must be fixed onto every patient to be evaluated by this method, and then connected to the monitoring equipment, which is rather time-consuming.

In addition, the connection must be so made that the patient remains free to perform the exercice requested for carrying out the evaluation. This often makes the connection rather complicated, thus making again the method time consuming to carry out.

OBJECTS AND SUMMARY OF THE INVENTION

An object of the present invention is to provide a connection kit for use in electrically connecting to a monitoring equipment a plurality of skin-markers and/or electrodes detachably fixed onto the body of a patient, which kit is very simple to install on a patient and/or to transfer from one patient already set with properly positioned skin-markers and electrodes, to another patient similarly set, thereby making it possible to carry out one or several successive physical evaluations in a much faster manner.

Another object of the invention is to provide a connection set of the above-mentioned type, which is so designed as to let the patient free to move in a given area of, say, 4×6 meters.

A further object of the invention is to provide a connection kit of the above-mentioned type, which is particularly well suited for use with an equipment for non-invasive evaluation of the flexibility of the spine of a patient, which equipment comprises a plurality of separate, dot-sized skin-markers each consisting of at least one LED attachable to the skin of the back of the patient and a set of surfaces electrodes for measuring the electromyographic (EMG) activities of the patient while he is performing a given exercice.

The connection kit according to the invention as broadly claimed hereinafter, comprises:

a) a connection box electrically connectable to a monitoring equipment in such a manner as to let the patient free to move in a given area;

b) a harness to be worn by the patient, said harness comprising a chest-piece and means on the chest piece to detachably mount the connection box (a);

c) at least one primary conductor cable having one end electrically connectable to the connection box and at least one other end provided with a connecting plug;

d) means for detachably fixing said at least one other end of the primary cable (c) at a given height onto the patient's back; and e) at least one secondary conductor cable having one end electrically connectable to the connecting plug provided at one of said at least one other end of said at least one primary cable (c), and at least one other end electrically connectable to at least one of the skin-markers and/or electrodes.

In practice, the electrical connection of the connection box to the monitoring equipment can be achieved by telemetry. Alternatively, this electrical connection can be achieved by means an "umbilical cord" long enough to let the patient free to move in the given area.

In accordance with a preferred embodiment of the invention, the means (d) for detachably fixing the other end(s) of the primary cable(s) onto the patient's back consists of a sticking pad having two opposite faces that are self-adhesive. In such a case, one face of the pad is sticked onto the patient's skin while its other face is used to stick the other end of the primary cable.

Alternatively, said fixation means may consist of a snap-connector including a male (or female) element attached to one face of a sticking pad whose other face is self-adhesive to the patient's skin, and a female (or male) element attached to the other end of the primary cable to be fixed.

In accordance with another preferred embodiment of the invention, the harness (b) also comprises a hip encircling belt and a pair of back-straps passing over the shoulders of the patient and extending bilaterally and symmetrically from the chest piece down to the hip encircling belt. If desired the harness (b) may further comprise a back-strap retainer connecting the straps at mid-height thereof, and a pair of lateral straps extending under the armpits bilaterally and symmetrically from the chest-piece to the adjacent back straps.

In this particular embodiment, the hip encircling belt, back straps and lateral straps of the harness (b) are preferably made detachable and adjustable in length to make the harness easier to fit to any patient and the means (d) for detachably fixing one other end(s) of the primary cable(s) (c) onto the back straps preferably consist of lengths or pieces of male and female fabric fasteners (VELCRO ®) respectively attached onto these one other ends and the back straps.

This particular embodiment makes the harness and electrical connection very easy to adjust to any size of patient.

When the connection kit is used in an equipment as disclosed in the above referenced Canadian patent application No. 548,627 which makes use of 24 skin-markers connected to a strober, and 8 EMG electrodes connected to an EMG-preamplifier and transmitter, the connection box (a) preferably incorporates the EMG-preamplifier and transmitter which are provided with a 25-pin connector outlet, and the strober which is provided with two 25-pin connector outlets. Then, the kit includes:

one primary Y-shaped EMG multi-wired conductor cable having its one end provided with a 25-pin connector connectable to the outlet of the EMG-preamplifier and transmitter and its two other ends each provided with a 8-contact plug, the one primary EMG conductor cable also including a grounding wire directly connectable to the patient skin;

two primary skin-markers conductor cables each having an outlet divided into three multi-wired branches, the one end of each of the primary skin-marker conductor cable being provided with a 25-pin connector connectable to one of the outlets of the strober, each of the other ends of the primary skin-marker conductors being provided with a 8-contact connecting plug;

two secondary EMG conductor cables each having an outlet divided into four bi-wired branches, the one end of each of the secondary EMG conductor cables being provided with a 8-contact plug connectable to the corresponding plug of one of the other ends of the primary EMG conductor cable, each of the other end of the secondary EMG conductor cables being provided with a pair of terminal clamps for fixation to an EMG surface-electrode; and six secondary skin-marker conductor cables each having an outlet divided into four bi-wired branches, the one end of each of the secondary skin-marker conductor cables being provided with a 8-contact plug connectable to the corresponding plug of one of the other ends of the primary skin-marker conductor cables, each of the other ends of the secondary skin-marker conductor cables being electrically connected to at least one LED to energize the same.

BRIEF DESCRIPTION OF THE DRAWINGS

The invention will be better understood upon reading of the following non restrictive description of a preferred embodiment thereof for use with an equipment for the evaluation of the flexibility of the spine of a patient as disclosed and claimed in the above referenced U.S. patent application Ser. No. 250,215, this description being given with reference with accompanying drawings in which:

FIG. 4 is a schematic representation of the wiring of the connection kits shown in FIGS. 3 and 4; and FIG. 5 is a perspective view of a skin-marker for use in the midline of the patient's back.

DESCRIPTION OF TWO PREFERRED EMBODIMENTS a) General Description of the Equipment To Be Used With the Connection Kit

Figure 1:
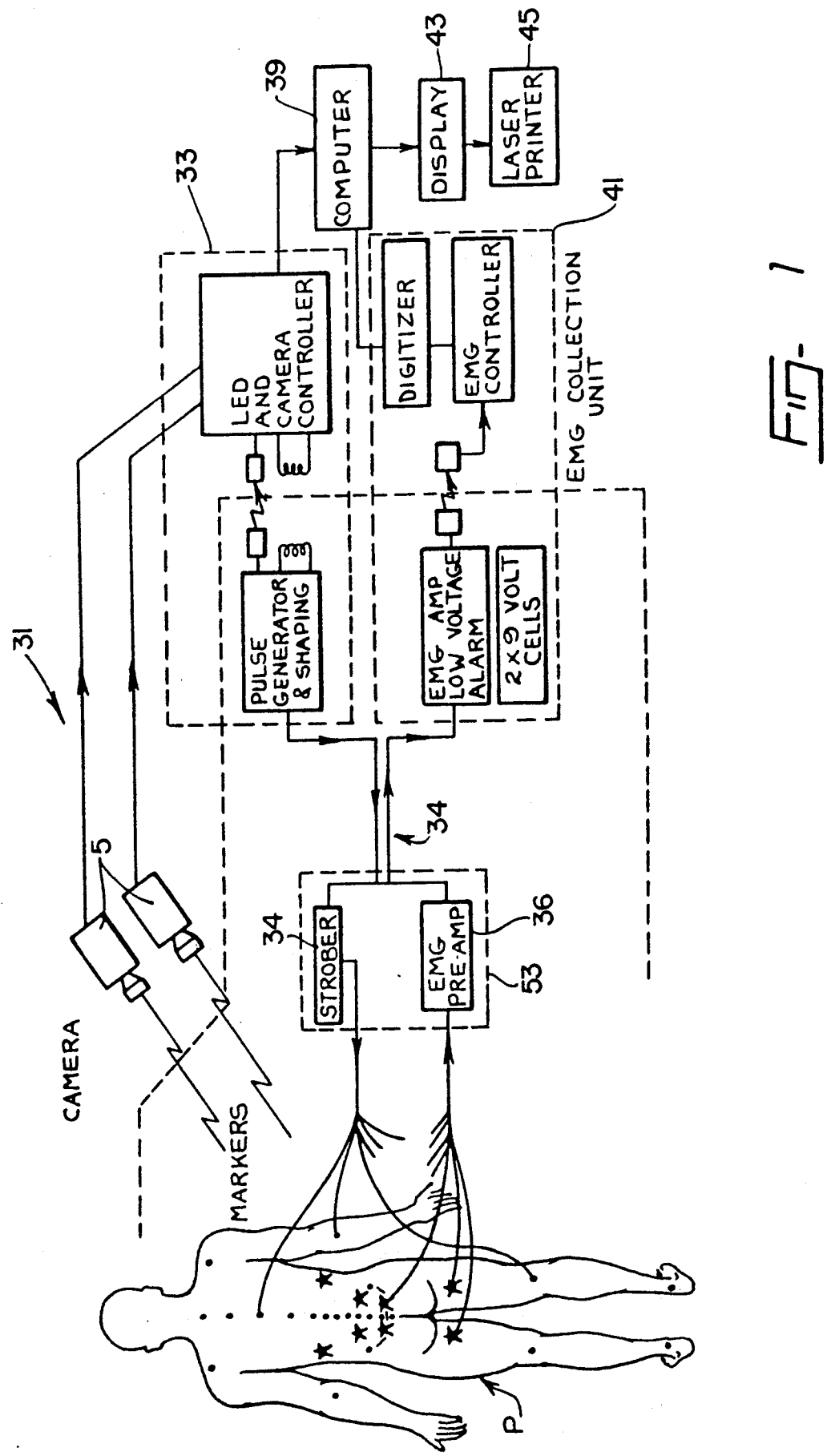
FIG. 1 is a schematic representation of the equipment disclosed and claimed in the above-mentioned Canadian patent application.

The non-invasive equipment 31 as shown in FIG. 1, is primarily designed to observe and record the spatial positioning of the spine of a patient "P" during one or more very specific exercises, such as executing lifts in the sagittal plane or laterally bending in the frontal plane. The geometry of the spine of the patient during the exercise is deduced by measuring the position of 24 dot-shaped, skin markers numbered 1 to 24 respectively, which are fixed on the patient as shown with round dots in FIGS. 1 and 2. Of the 24 markers, twelve are distributed along the back above the spine.

The markers 1 to 24 are, in fact, small light-emitting diodes (LEDs) whose firing are controlled by a monitoring unit 33 via a strober 34, and tracked by two spaced-apart cameras 35.

Figure 2:
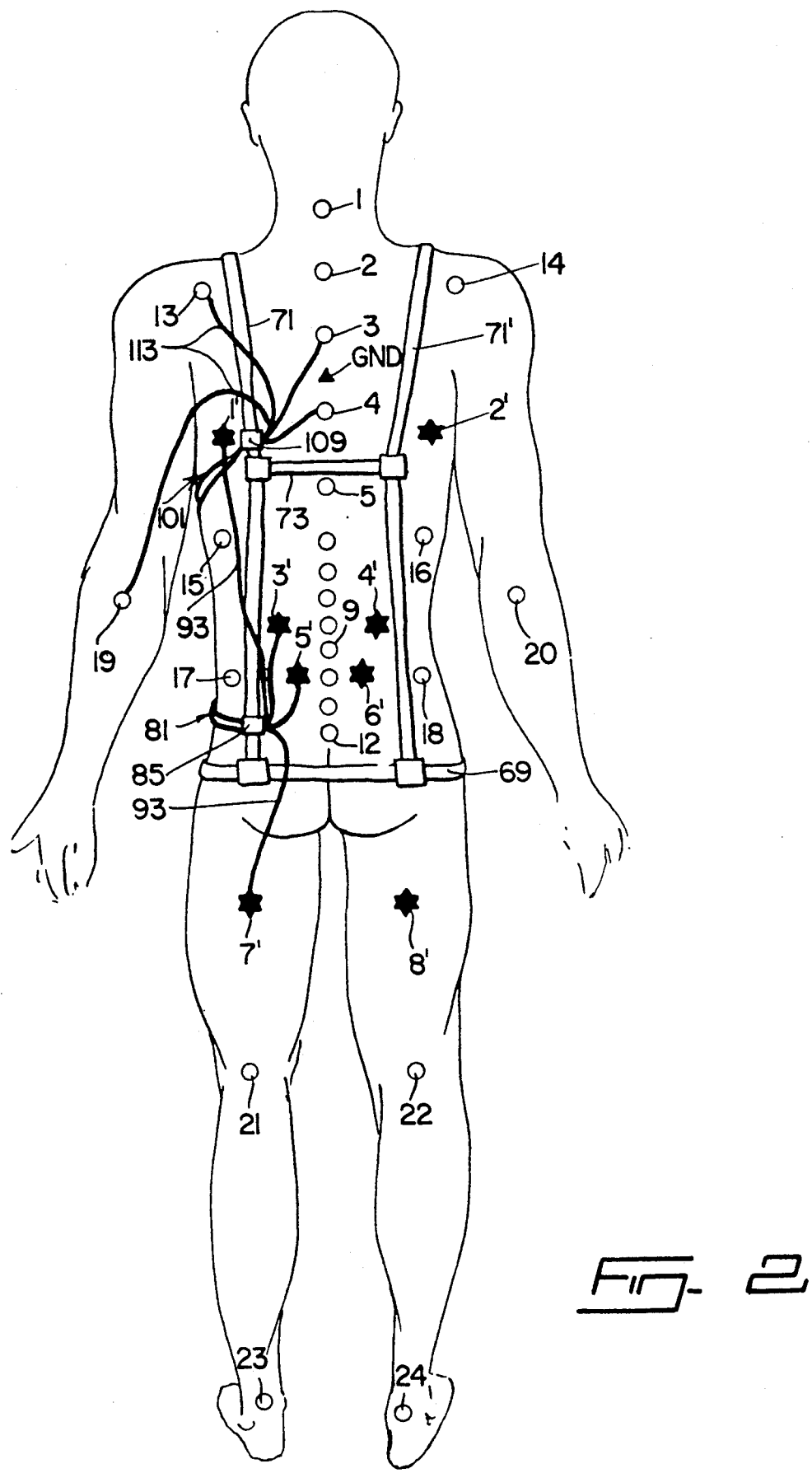
FIG. 2 is a schematic representation of a patient back, showing the particular position of the skin-markers and EMG electrodes used with the equipment shown in FIG. 1.

As better shown in FIG. 2, the uppermost LED 1 in the patient's midline is preferably fixed on the spinous process of cervical vertebra $C_7$ or $T_1$ while the lowermost LED 12 is fixed on a sacral vertebra, preferably $S_2$. Two other LEDs 5 and 9 are also preferably positioned on the spinous process of thoracic $T_{11}$ and lumbar vertebra $L_4$, the other LEDs being merely put in between at regular interval. As a matter of fact, once some spaced-apart LEDs are set, the positions of the other LEDs with respect to the anatomical landmarks, may be easily calculated from normalized anatomical tables.

Two of the remaining 12 markers, namely those numbered 17 and 18 in FIG. 2, are and must be positioned onto the skin of the back of the patient in a bilateral and symmetrical manner on the crest of the patient's ilium, at height substantially halfway between lumber vertebrae $L_4$ and $L_5$ (which usually correspond to the height of LEDs 9 and 10 in the patient's midline).

The ten remaining markers are merely used to track with the cameras 35 the general position of the patient while he is flexing forward. These remaining markers are respectively fixed bilaterally and symmetrically onto the patient's shoulder at height substantially halfway between cervical vertebra $L_7$ and thoracic vertebra $T_3$ (see LEDs 13 and 14), on the patient's back at height substantially halfway between thoracic vertebra $T_{11}$ and lumbar vertebra $L_1$ (see LEDs 15 and 16), and on the patient's appendages (i.e. his legs and arms), above his elbows (see LEDs 19 and 20), below his knees (see LEDs 21 and 22) and at his Achilles tendons (see LEDs 23 and 24).

The three-dimensional co-ordinates of each marker are reconstructed by a computer 39 from the data generated by the two cameras 35. As the data is collected by the cameras at a speed of 180 sets of 24 markers per second, these can be combined to improve accuracy and still maintain an acceptable dynamic range at approximately 12 images per second.

By suitably processing the respective positions of the twelve markers 1 to 12 fixed in the midline of the patient's back when the patient is, for example, flexing forward, one may easily determine the angle of forward flexion α of the trunk of the patient as a function of time.

This angle α which is indicative of the combined motion of both the hip and spine of the patient, can be displayed at 43 and plotted with a laser printer 45. Simultaneously to the above processing, the recorded positions of the two skin-markers 17 and 18 symmetrically fixed on the crest of the patient's ilium are processed by the computer 39 with the recorded position of the skin-marker 12 fixed on the sacral vertebra $S_2$, to determine the angle of rotation "h" of the hip as a function of time. This angle "h" which is indicative of the hip motion of the patient, can be derived from the motion of the plane (see the dotted triangle on the back of the patient in FIG. 1) defined by the abovementioned three markers 12, 17 and 18.

Since the total motion characterized by the angle is due to the combined motion of both spine and hip, the spine motion can be deduced by measuring the motion of the hip and substraction it from the motion of the trunk. In other words, the substraction of angle "h" from angle permit to determine the actual contribution of the spine to the total flexion of the patient as a function of time. This contribution, which is hereinafter expressed as angle "s" is indicative of the spine motion of the patient.

The values of angles α, "h" and "s" that are so obtained are further processed by the computer 39 to calculate the relative variations of "h" and "s" versus α. The variations which are respectively indicative of the ranges of hip and spine motions in the sagittal plane, are plotted and displayed and may be used as accurate diagnosis tools by anyone skilled in the medical art to evaluate the flexibility of the spine and detect the presence of a potential mechanical injury in this spine. This diagnosis can very easily be made by comparing with each other the plots obtained for a given patient and, if necessary, comparing these plots with "standard plots" obtained from a group "normal" patients to determine any discrepancy or singularity.

In practise, the determination of the ranges of hip and spine motion in the sagittal plane, is sufficient as such to establish or confirm a diagnosis. However further informations such as the range of variation of the lumbosacral angle Ψ, the percentage arc elongation and/or the EMG activities of the patient's muscles, may also be obtained with the safe equipment to confirm, complete and cross-check the basic date already obtained.

As shown in FIGS. 1 and 2, the measurement of the electromyographic (EMG) activities of the patient's muscles can be carried out by detachably fixing a set of eight surface electrodes 1' to 8' (shown as "stars" on the patient "P" in FIGS. 1 and 2) bilaterally on the latissimus dorsi below scapula, the longissimus lumborum at vertebra $L_3$, the multifidus at $L_5$ and the harmstring semitensinosus. The ground GND may be fixed on the midline, between LED 3 and LED 4. Alternatively, the EMG data may be collected bilaterally on the multifidus (2 cm off the midline at $L_5$ level). on the iliocostalis and longissiums lumborum (at 4 cm off the midline at $L_3$), on the external obliques the triangle of Petit, on the latissimus dorsi at $T_5$ and on the rectus abdominis at the $L_3$ level. The raw EMG signals that are recorded, are pretreated in a preamplifier 36, and transmitted to a treatment unit 41 in which the preamplified signals are band-filtered (5 Hz to 300 Hz), digitized at 1 KHz and rectified. Then, the signals are integrated by the computer 39 to determine the magnitude of activity of every muscle and the integrated signals plotted as a function of time.

Figure 3A:
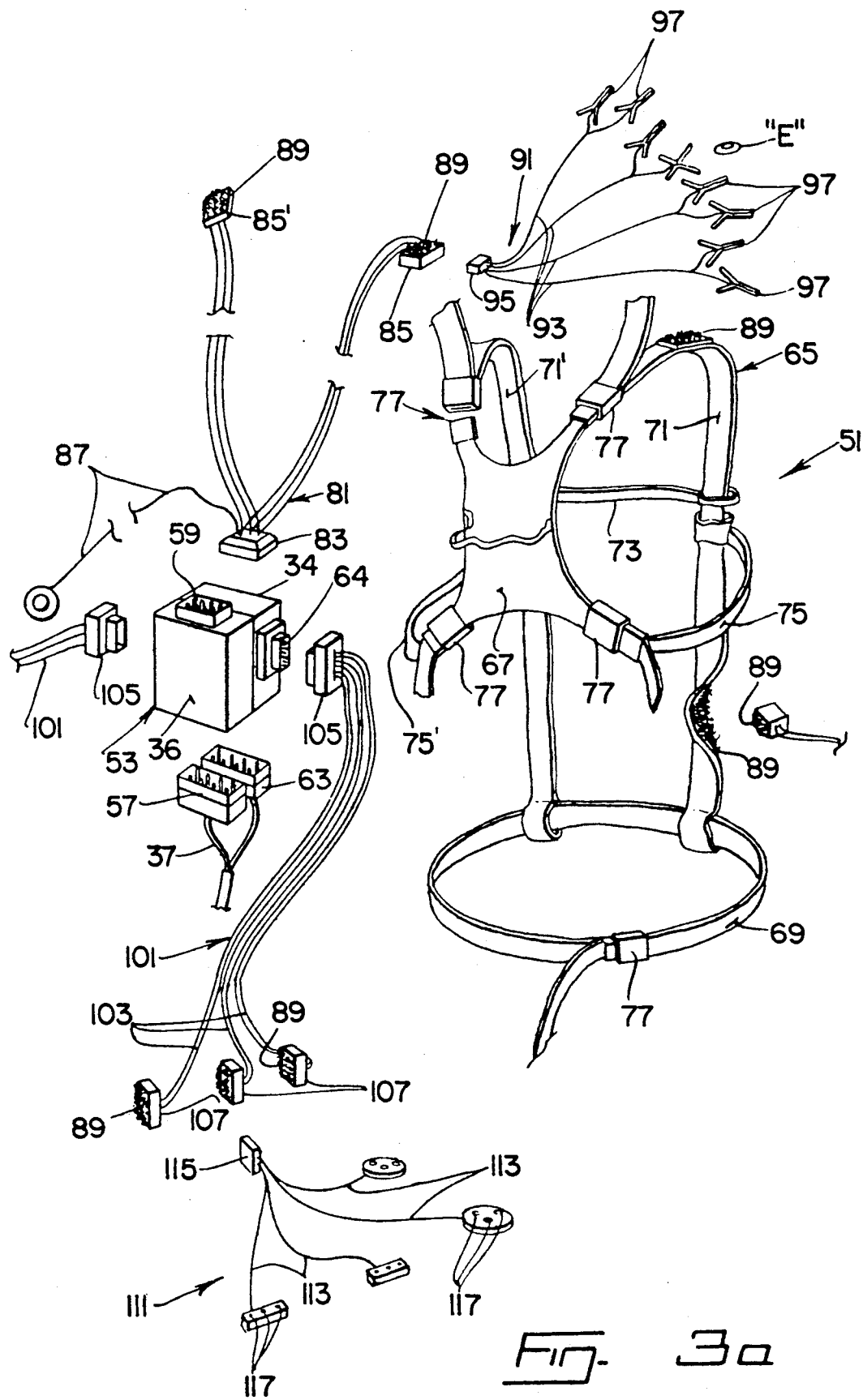
FIG. 3a is an exploded view of a connection kit according to the invention, for use with the equipment shown in FIG. 1.

The plots obtained on the left and right sides of the patient may be compared to detect any discrepancy, and this information as well as the general muscle activity as reflected by all of the EMG plots may be used as a further information to detect the presence of a potential mechanical injury in the lumbar spine of the patient.

b) Description of a First Embodiment of a Connection Kit According to the Invention The connection kit 51 according to the first embodiment of the invention as shown in FIGS. 2, 3a and 4, is intended to be used for electrically connecting the skin-markers 1 to 24 and the EMG surface electrodes 1' to 8' detachably fixed onto the body of the patient "P", to the monitoring equipment 31 in such a manner as to let the patient free to move and perform the requested exercise in the sagittal plane.

The kit 51 is also intended to make the requested connection very simple to carry out and very easy to adjust to any size of patient, thereby making it possible to process more patients with the same basic equipment within a given period of time.

As better shown in FIGS. 1, 3a and 4, the kit 51 comprises a connection box 53 electrically connected to the LED-monitoring unit 33 and EMG-signal treatment unit 41 of the equipment 31 via an umbilical cord 37 of such a length as to let the patient free to move in the given area. Alternatively, the connection may be achieved by telemetry or by any other telecommunication system of the same type, known to those skilled in this art. The connection box 53 incorporates the EMG-preamplifier and transmitter 36 which is provided with a pin-connector inlet 55 connectable to a plug 57 at the end of the cord 37, and a 25-pin connector outlet 59. The box 53 also incorporates the strober 34 which is provided with a pin-connector 61 connectable to a plug 63 at the end of the cord 37, and two 25-pin connector outlets 64. The plugs 57 and 63 are of course respectively connected to the units 41 and 33.

The kit 51 also comprises a harness 65 to be worn by the patient. The harness 65 comprises a chest-piece 67, a hip encircling belt 69 and a pair of back-straps 71, 71' passing over the shoulders of the patient and extending bilaterally and symmetrically from the chest piece 67 down to the hip-encircling belt 69. The harness 65 further comprises a back-strap retainer 73 connecting the straps 71, 71' at mid-height thereof in the patient's back, and a pair of lateral straps 75, 75' extending under the armpits bilaterally and symmetrically from the chest-piece 67 to the adjacent back straps 71, 71'. All of the hip-encircling belt 69, back-straps 71, 71' and lateral straps 75, 75' of the harness are advantageously provided with snap-in buckles 77 making them detachable and adjustable in length to fit any size of patient.

Means are provided on the chest piece 67 to detachably mount the connection box 53. These mounting means may consist of a hook, a pocket or a mere elastic band 79 as shown in FIG. 3.

The connection kit 51 further comprises a double set of conductor cables to be connected in line, to make the installation, adjustment and connection of the pretreatment circuit in the box 53 to the markers 1 to 24 and the electrodes 1' to 8', very easy to perform.

In the embodiment shown in FIGS. 2 and 3, this set of conductor cables comprises a primary Y-shaped EMG multi-wired conductor cable 81 having an inlet end provided with a 25-pin connector 83 connectable to the outlet 59 of the EMG-preamplifier and transmitter 36, and two outlet ends each provided with a 8-contact plug 85, 85' that can be of the snap-in type ("telephone" plug). The primary EMG conductor cable 81 also includes a grounding wire 87 directly connectable to the patient skin (see the triangle GND in FIG. 2).

Means are provided for detachably fixing each plug 85, 85' at the outlet ends of the primary cable 81 at any given height onto the back-straps 71, 71'. These means preferably consist of pieces or bands of interlocking elements 89 such as VELCRO (trade mark) respectively attached (by gluing or sewing) onto the bodies of the plugs 85, 85' and portions of the lengths of the back-straps 71. 71'. VELCRO ® is well known in the trade and its installation and use (from "male" and "female" pieces to be matched) will not be described in greater detail hereinafter.

The primary EMG cable 81 is intended to be used with two secondary EMG conductor cables 91, 91' each having an outlet divided into four bi-wired branches 93. The inlet of each secondary EMG conductor cable 91, 91' is provided with a 8-contact plug 95, 95' connectable to the corresponding plug 85, 85' at the outlet of the primary EMG conductor cable 81. Each of the other ends of each secondary EMG conductor cable 91, 91' is provided with a pair of terminal clamps 97 for fixation to an EMG surface-electrode "E". With such a double connection to each EMG electrode "E" and the presence of a grounding wire 87 directly connected to the patient skin, every EMG measurement is carried out in a differential manner, thereby making the recorded data much more accurate.

The set of conductor cables of the kit 51 shown in FIGS. 3 and 4 also comprises two primary, ribbon-shaped skin-markers conductor cables 101 each having an outlet divided into three multi-wired branches 103. The inlet of each of these primary skin-marker conductor cables 101 is provided with a 25-pin connector 105 connectable to one of the outlets 65 of the strober 34. Each of the three outlets of each primary skin-marker conductor 101 is provided with a 8-contact connecting plug 107 that can be of the snap-in type ("telephone" plug).

As for plugs 85, 85', means are provided for detachably fixing each of these plugs 107 at any given height onto the back-straps 71, 71'. These means may also consist of VELCRO ® fasteners 89, as explained hereinabove for cables 81.

Each primary skin-markers conductor cables 101 is intended to be used with three secondary skin-marker conductor cables 111 each having an outlet divided into four bi-wired branches 113. The inlet of each secondary skin-marker conductor cable 111 is provided with a 8-contact plug 115 connectable to the corresponding plug 107 of one of the outlet of one of the primary skin-marker conductor cables 101. Each of the four outlets of each secondary skin-marker conductor cable 111 is electrically connected to at least one skin-marker 1 to 24 (see FIG. 2) to energize the same.

As better shown in FIGS. 3 and 5, the skin-markers connected to the end of each double wire 113 of the secondary conductor cable 111 preferably comprise three separate LEDs 117 or, alternatively, one single LED provided with one single epoxy cover but with three separate heads connected in series onto the same silicon base 119. The advantage of using three LEDs (or a single LED with three heads) is to provide enough light to allow the cameras 35 to track the motion of the spine. This is the very reason why the LEDs are preferably mounted in series (if one is faulty, the corresponding marker will be off and thus immediately detected by the cameras).

Each skin-marker may be stuck onto the patient's skin with a sticking pad 121 having both of its faces adhesive.

Advantageously, the skin-markers intended to be stuck onto the spinous processes of the patient's spine must be separate and as small as possible. It is indeed compulsory that the markers may freely follow any motion or stretching of the patient's back without being affected by the muscular activity of this back, in order to give a true and real indication of the actual position of the spine. If the markers were larger, they would extend on both sides of the epiphysis of each vertebrae, along which extends a very active muscle called multifidus. Of course, this muscle "moves" on its own when the spine moves and affects the orientation of the large sensors fixed thereto. Therefore, if the patient while he was performing an exercice, had for any reason a muscular spasm, this motion would be sensed by the adjacent goniometer as a spinal motion and would create a very substantial error in the displayed data.

This particular requirement for the skin-markers stuck onto the patient's spine to be small, is much less important for the other markers to be stuck onto the shoulders or appendages, as the muscular support there is much larger.

Figure 3B:
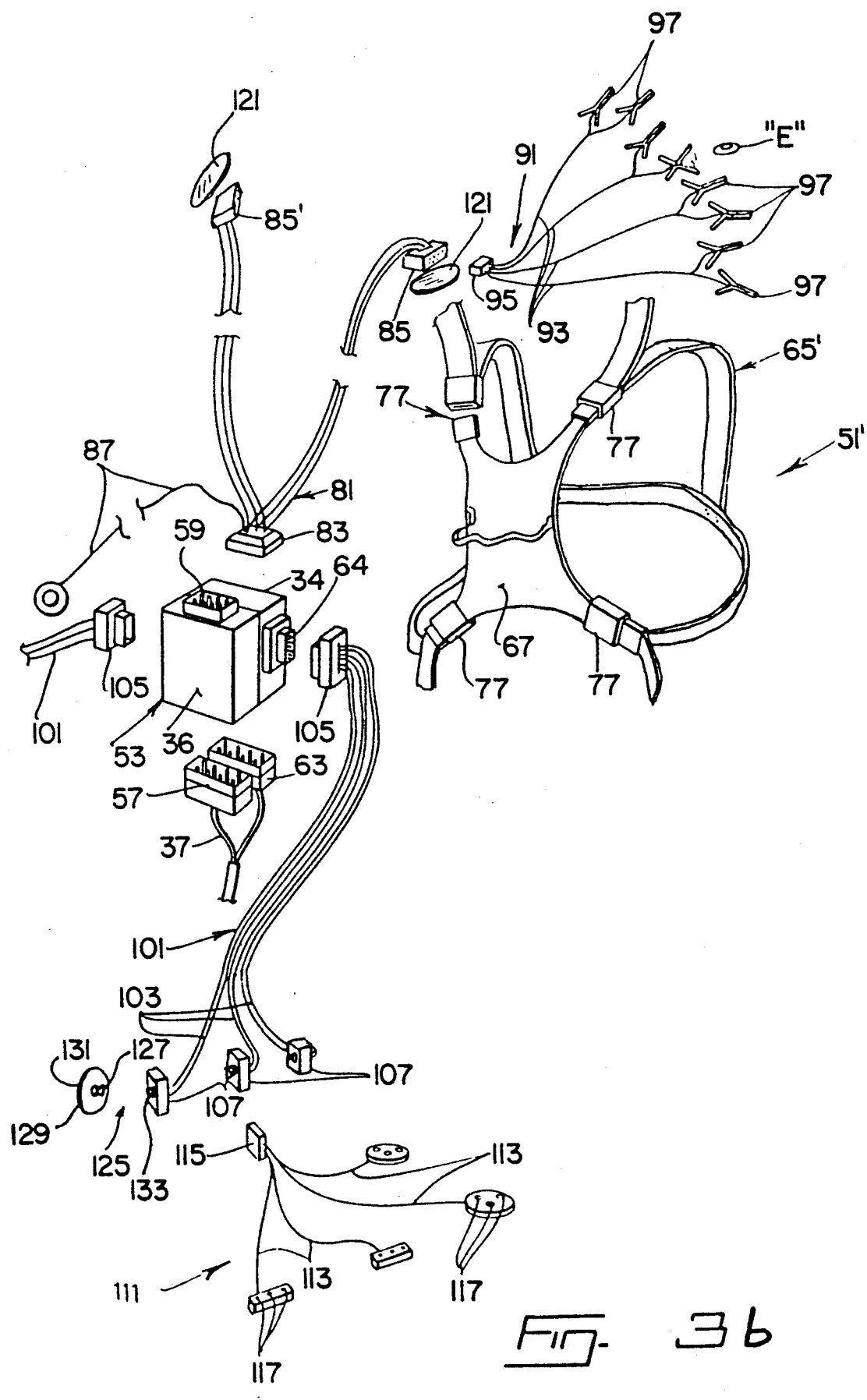
FIG. 3b is an exploded view of another connection kit according to the invention, for use with the equipment shown in FIG. 1.

Advantageously also, jumpers 123 (see FIG. 4) may be used between plugs 59 and 83 and each pair of plugs 65 and 105 to protect the plating of the pins of the connectors 59 and 65 and make them to last longer.

c) Description of a Second Embodiment of a Connection for Kit according to the Invention The connection kit 51' according to the second embodiment of the invention as shown in FIG. 3b is very similar to the one previously described. It comprises the same wirings and "works" substantially in the same manner. For this reason, the same reference numerals as in FIG. 3a have been used in FIG. 3b to identify the same structural elements.

As a matter of fact, the connection kit 51' differs from the kit 51 only in that:

its harness 65' is shaped as a brassiere, with the chest piece 67 held centrally onto the patient's chest by means of small shoulder and waist's encircling straps adjustable in length at 77; and the means for detachably fixing each plug 85, 85' or 107 of the primary EMG or skin-markers conductor cables 81 or 101 onto the patient's back consists of a sticking pad 121 as shown in FIG. 5, having both of its opposite faces self-adhesive, or, alternatively, of a snap connector 125 including a male element 127 attached to one face of a sticking pad 129 whose other face 131 is self-adhesive to the patient's skin, and a female element 133 attached to the plug to be fixed.

d) Advantages of the Connection Kit According to the Invention

The kits 51 or 51' according to the invention as disclosed hereabove are particularly interesting in that they are both very simple in structure and efficient in use. They make it possible for the pretreatment circuitry included into the connection box 53, namely the strober 34 and EMG preamplifier 36, to be as closed as possible to the skin-markers 1 to 24 and EMG surface electrodes 1' to 8', thereby making the transmission and control much more efficient and reliable. They also make it possible for the pretreatment circuitry in the box 53, which circuitry is rather expensive, to be very easily transferred from one harnessed patient to another, thereby reducing the processing cost of several patients in a row. They further make the adjustment of the connection cables and cords from one patient to another very easy to perform, as it includes two distinct groups of conductor cables to be connected in line, namely primary and secondary conductor cables, which are both easy to plug in and to adjust (the plugs of the primary conductor cables being indeed very easily to adjust at any desired height either along the back-straps 71, 71' or with the adhesive pads 121 or snap connectors 125). In addition, they make the overall operation of the equipment 31 much easier to carry out, thereby making it more profitable to everyone.

It is worth repeating that the connection kits 51 and 51' disclosed hereinabove are not exclusively restricted to be used with the equipment 31 disclosed hereinabove. As a matter of fact, these kits can be used with any kind of equipment making use of skin-markers and/or electrodes that must be connected to a monitoring equipment, like those disclosed and claimed in the patents listed in the preamble of the present specification, or those others commonly used in most of the hospitals.

What is claimed is:

1. A connection kit for use with an equipment for non-invasive evaluation of the flexibility of the spine of a patient, said equipment comprising a plurality of separate, dot-sized skin-markers each consisting of at least one LED attachable to the skin of the back of the patient and a set of surface electrodes for measuring the electromyographic (EMG) activities of the patient while he is performing a given exercice, said kit comprising:
   a) a connection box electrically connectable to a monitoring equipment in such a manner as to let the patient free to move in the given area, said connection box (a) incorporating an EMG-amplifier and transmitter provided with a 25-pin connector outlet and a strober provided with two 25-pin connector outlets,
   b) a harness to be worn by the patient, said harness comprising a chest-piece and means on the chest piece to detachably mount the connection box (a);
   c) a set of primary conductor cables each having one end electrically connectable to the connection box and at least one other end provided with a connecting plug; said set of primary cables including:
      one primary Y-shaped EMG multi-wired conductor cable having its one end provided with a 25-pin connector connectable to the outlet of the EMG-amplifier and transmitter and its two other ends each provided with a 8-contact plug, said one primary EMG conductor cable also including a grounding wire directly connectable to the patient skin; and
      two primary skin-marker conductor cables each having an outlet divided into three multi-wired branches, the one end of each of said primary skin-marker conductor cables being provided with a 25-pin connector connectable to one of the outlets of the strober, each of the other ends of said primary skin-marker conductors being provided with a 8-contact connecting plug;
   d) means for detachably fixing each of said other ends of said primary cables (a) at a given height onto the patient's back; and
   e) another set of secondary conductor cables, said other set including,
      two secondary EMG conductor cables each having an outlet divided into four bi-wired branches, the one end of each of said secondary EMG conductor cables being provided with a 8-contact plug connectable to the corresponding plug of one of the other ends of the primary EMG conductor cables, each of the other end of said secondary EMG conductor cables being provided with a pair of terminal clamps for fixation to an EMG surface-electrode; and
      six secondary skin-marker conductor cables each having an outlet divided into four bi-wired branches, the one end of each of said secondary skin-marker conductor cables being provided with a 8-contact plug connectable to the corresponding plug of one of the other ends of the primary skin-marker conductor cables, each of the other ends of said secondary skin-marker conductor cables being electrically connected to at least one Led to energize the same.

2. A connection kit as claimed in claim 1, wherein: the harness (b) also comprises a hip encircling belt and a pair of back-straps passing over the shoulders of the patient and extending bilaterally and symmetrically from the chest piece down to the hip encircling belt; and
   said means (d) for detachably fixing said at least one other end of said at least one primary cable (c) onto the patient's back consist of pieces of male and female fabric fasteners respectively attached onto said at least one other end, and said back straps.

3. A connection kit as claimed in claim 2, wherein: the harness (b) further comprises a back-strap retainer connecting the back-straps at mid-height thereof, and a pair of lateral straps extending under the armpits bilaterally and symmetrically from the chest-piece to the adjacent back-straps; and
   the hip encircling belt, back-straps and lateral straps of the harness (b) are detachable and adjustable in length.

4. A connection kit as claimed in claim 3, further comprising an umbilical cord to electrically connect the connection box (a) to the monitoring equipment, said umbilical cord being of such a length as to let the patient free to move in said given area.

5. A connection it as claimed in claim 1, wherein said means (d) for detachably fixing said other ends of said primary cables (c) onto the patient's back consist of sticking pads having two opposite faces that are self-adhesive to the patient's skin and to said other ends respectively.

6. A connection kit as claimed in claim 5, further comprising an umbilical cord to electrically connect the connection box (a) to the monitoring equipment, said umbilical cord being of such a length as to let the patient free to move in said given area.

7. A connection kit as claimed in claim 1, wherein said means (d) for detachably fixing said other ends of said primary cables (c) onto the patient's back consist of snap connectors including male and female elements attached to a sticking pad capable of adhering to the patient's skin and to said other ends, respectively.

8. A connection kit as claimed in claim 7, further comprising an umbilical cord to electrically connect the connection box (a) to the monitoring equipment, said umbilical cord being of such a length as to let the patient free to move in said given area.

* * * * *